United States Patent [19]

Cason-Smith et al.

[11] Patent Number: 5,250,730
[45] Date of Patent: Oct. 5, 1993

[54] PROCESS FOR PRODUCING HYDROXY TERMINATED NITRAMINES

[75] Inventors: Donna M. Cason-Smith, Columbia; Horst G. Adolph, Burtonsville, both of Md.

[73] Assignee: The United States of America as represented by the Secretary of the Navy, Washington, D.C.

[21] Appl. No.: 912,416

[22] Filed: Jul. 13, 1992

[51] Int. Cl.$^5$ ............................................. C07C 241/00
[52] U.S. Cl. ................................................ 564/109
[58] Field of Search .............................. 564/107, 109

[56] References Cited

PUBLICATIONS

Reed, Jr., "Tetramethylenetrinitramine Trifluoroacetates", *J. Amer. Chem. Soc.*, vol. 78, No. 4, (Feb. 20, 1956), pp. 801–804.

Solomons, *Organic Chemistry*, 2nd Ed., John Wiley and Sons, New York, (1980), pp. 768–771.

*Primary Examiner*—Glennon H. Hollrah
*Assistant Examiner*—P. O'Sullivan
*Attorney, Agent, or Firm*—John D. Lewis; Roger D. Johnson

[57] ABSTRACT

A process by which 1,7-dihydroxy-2,4,6-trinitro-2,4,6-triazaheptane or 1,9-dihydroxy-2,4,6,8-tetranitro-2,4,6,8-tetraazanonane is produced by hydrolyzing 1,7-diacetoxy-2,4,6-trinitro-2,4,6-triazaheptane or 1,9-diacetoxy-2,4,6,8-tetranitro-2,4,6,8-tetraazanonane with concentrated aqueous hydrochloric acid comprising from 28 to 32 weight percent of hydrogen chloride with the remainder being water.

5 Claims, No Drawings

PROCESS FOR PRODUCING HYDROXY TERMINATED NITRAMINES

BACKGROUND OF THE INVENTION

This invention relates to nitramines and more particularly to nitramines having hydroxy functional groups.

1,7-Dihydroxy-2,4,6-trinitro-2,4,6-triazaheptane (3ND) has been prepared from 1,7-diacetoxy-2,4,6-trinitro-2,4,6-triazaheptane (BSX) according to a method disclosed by [J. Amer. Chem. Soc. 1956,801] shown in the following equation:

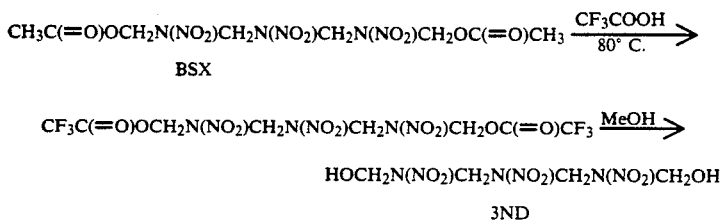

While this method does provide access to 3ND, both the mono and bis(trifluoroacetates) are formed during the trifluoroacetolysis and are difficult to separate. After purification, only 45% of the bis(trifluoroacetate) was obtained from BSX. Purification of this intermediate is necessary to obtain 3ND of good quality because 3ND is unstable in solution and cannot be purified easily. The yield of the bis(trifluoroacetate) can be increased to 60% by repeating the trifluoroacetolysis step on the crude initial reaction product. The methanolysis of the pure (trifluoroacetate) to 3ND proceeds quantitatively. The major disadvantages of this procedure are that large amounts of expensive trifluoroacetic acid and repeated recrystallizations are required. It involves at least four separate steps (2 acetolyses, 1 recrystallization, 1 methanolysis). The same problems will exist if this process is used to prepare 1,9-dihydroxy-2,4,6,8-tetranitro-2,4,6,8-tetraazanonane from 1,9-diacetoxy-2,4,6,8-tetranitro-2,4,6,8-tetraazanonane.

Therefore, it would be desirable to provide a new less expensive, more efficient, and easier method of producing 1,7-dihydroxy-2,4,6-trinitro-2,4,6-triazaheptane or 1,9-dihydroxy-2,4,6,8-tetranitro-2,4,6,8-tetraazanonane.

SUMMARY OF THE INVENTION

Accordingly, an object of this is to provide a more efficient method of producing 1,7-dihydroxy-2,4,6-trinitro-2,4,6-triazaheptane or 1,9-dihydroxy-2,4,6,8-tetranitro-2,4,6,8-tetraazanonane.

Another object of this invention is to provide a less expensive method of producing 1,7-dihydroxy-2,4,6-trinitro-2,4,6-triazaheptane or 1,9-dihydroxy-2,4,6,8-tetranitro-2,4,6,8-tetraazanonane.

A further object of this invention is to provide a method which can be more easily scaled up to produce 1,7-dihydroxy-2,4,6-trinitro-2,4,6-triazaheptane or 1,9-dihydroxy-2,4,6,8-tetranitro-2,4,6,8-tetraazanonane.

Yet, another object of this invention is to provide a method of producing 1,7-dihydroxy-2,4,6-trinitro-2,4,6-triazaheptane or 1,9-dihydroxy-2,4,6,8-tetranitro-2,4,6,8-tetraazanonane in greater yield.

These and other objects of this invention are achieved by providing:

a method of producing dihydroxy terminated nitramines comprising contacting a diacetoxy terminated nitramine that is 1,7-diacetoxy-2,4,6-trinitro-2,4,6-triazaheptane or 1,9-diacetoxy-2,4,6,8-tetranitro-2,4,6,8-tetraazanonane with a concentrated aqueous hydrochloric acid comprising from 28 to 32 percent by weight hydrogen chloride with the remainder being water until the diacetoxy terminate nitramine is hydrolyzed to form the corresponding dihydroxy terminated nitramine 1,7-dihydroxy-2,4,6-trinitro-2,4,6-triazaheptane or 1,9-dihydroxy-2,4,6,8-tetranitro-2,4,6,8-tetraazanonane, respectively.

DETAILED DESCRIPTION OF THE PREFERRED EMBODIMENT

As a substitute for the expensive trifluoroacetolysis process for synthesizing hydroxy terminated nitramines, many standard hydrolysis procedures were tried and failed. For example, direct hydrolysis of 1,7-diacetoxy-2,4,6-trinitro-2,4,6-triazaheptane using trifluoromethanesulfonic acid ($CF_3SO_3H$), sulfuric acid ($H_2SO_4$), and trifluoroacetic acid ($CF_3COOH$) in various concentrations either failed to produce 1,7-dihydroxy-2,4,6-trinitro-2,4,6-triazaheptane or produced it in low yield with impurities which made it unsuitable for use as a monomer for producing energetic polymers. Transesterification of 1,7-diacetoxy-2,4,6-trinitro-2,4,6-triazaheptane also failed to give the desired product. Hydrolysis using a base is not available because the product 1,7-dihydroxy-2,4,6-trinitro-2,4,6-triazaheptane is destroyed by bases. All of the above limitations apply equally to the hydrolysis of 1,9-diacetoxy-2,4,6,8-tetranitro-2,4,6,8-tetraazanonane to produce 1,9-dihydroxy-2,4,6,8-tetranitro-2,4,6,8-tetraazanonane.

Surprisingly, it has now been found that concentrated aqueous hydrochloric acid comprising preferably from 28 to 32, more preferably from 29 to 31, and still more preferably about 30 weight percent of hydrogen chloride, with the remainder being water, can be used to hydrolyze diacetoxy terminated nitramines to produce the corresponding dihydroxy terminated nitramines. Specifically, in the process of this invention, the concentrated aqueous hydrochloric acid hydrolysis is used to produce 1,7-dihydroxy-2,4,6-trinitro-2,4,6-triazaheptane, $HOCH_2N(NO_2)CH_2N(NO_2)CH_2N(NO_2)CH_2OH$, from 1,7-diacetoxy-2,4,6-trinitro-2,4,6-triazaheptane, $CH_3C(=O)OCH_2N(NO_2)CH_2N(NO_2)CH_2N(NO_2)CH_2OC(=O)CH_3$, or to produce 1,9-dihydroxy-2,4,6,8-tetranitro-2,4,6,8-tetraazanonane, $HOCH_2N(NO_2)CH_2N(NO_2)CH_2N(NO_2)CH_2N(NO_2)CH_2OH$, from 1,9-diacetoxy-2,4,6,8-tetranitro-2,4,6,8-tetraazanonane, $CH_3C(=O)OCH_2N(NO_2)CH_2N(NO_2)CH_2N(NO_2)CH_2N(NO_2)CH_2OC(=O)CH_3$.

The weight percentage ranges for hydrogen chloride in the concentrated aqueous hydrochloric acid are critical. Concentrated hydrochloric acid (37 weight percent hydrogen chloride) failed to hydrolyze 1,7-diacetoxy-2,4,6-trinitro-2,4,6-triazaheptane to 1,7-dihydroxy-2,4,6-trinitro-2,4,6-triazaheptane. Aqueous hydrochloric acid solutions containing 20 and 25 weight percent of hydrogen chloride produced 1,7-dihydroxy-2,4,6-trinitro-2,4,6-triazaheptane in low yield with undesirable impurities. However, concentrated aqueous hydrochloric acid containing 30 weight percent hydrogen chloride was used to hydrolyze 1,7-diacetoxy-2,4,6-trinitro-2,4,6-triazaheptane to produce 1,7-dihydroxy-2,4,6-trinitro-2,4,6-triazaheptane in 75 percent yield. The product was sufficiently pure to be used as a monomer for energetic polymers without a purification step.

The concentrated aqueous hydrochloric acid is mixed with the dry 1,7-diacetoxy-2,4,6-trinitro-2,4,6-triazaheptane or 1,9-diacetoxy-2,4,6,8-tetranitro-2,4,6,8-tetraazanonane starting material. Preferably, no solvents are used. The mixture is agitated (e.g., stirred) during the hydrolysis. The hydroysis is preferably run at ambient temperature. High temperatures may result in lower yields due to decomposition of the dihydroxy terminated nitramine product.

After the hydrolysis, the crude 1,7-dihydroxy-2,4,6-trinitro-2,4,6-triazaheptane or 1,9-dihydroxy-2,4,6,8-tetranitro-2,4,6,8-tetraazanonane product is collected (e.g., by filtration) and washed with water. Although the crude 1,7-dihydroxy-2,4,6-trinitro-2,4,6-triazaheptane or 1,9-dihydroxy-2,4,6,8-tetranitro-2,4,6,8-tetraazanonane will contain a few weight percent of RDX as an impurity, the crude product may be used without further purification as a comonomer in energetic polymers for explosive binders. This is important since recrystalization of the crude product would reduce the yield because the nitramine diol product is unstable in solution and cannot be purified easily.

One utility for 1,7-dihydroxy-2,4,6-trinitro-2,4,6-triazaheptane and for 1,9-dihydroxy-2,4,6,8-tetranitro-2,4,6,8-tetraazanonane is as comonomers with a fluorodiol such as 2,2,3,3,4,4,5,5-octafluorohexane-1,6-diol, 2,4,4,5,5,6,6-heptafluoro-2-trifluormethyl-3-oxaheptane-1,7-diol, or 2,2,4,4,5,5,7,7-octafluoro-3,6-dioxoctane-1,8-diol. A mixture of 1,7-dihydroxy-2,4,6-trinitro-2,4,6-triazaheptane or 1,9-dihydroxy-2,4,6,8-tetranitro-2,4,6,8-tetraazanonane, a fluorodiol, and formaldehyde can be reacted in the presence of an acidic condensing agent such as boron trifluoride etherate. The resulting polymer is a polyformal having fluorodiol and nitraminediol units incorporated in the backbone (see example 4). The polyformal can be cured with conventional crosslinking agents such as aromatic dissocyanates (see example 5).

The general nature of the invention having been set forth the following example 1 is present as a specific illustration thereof. It will be understood that this invention is not limited to this specific example, but is susceptible to various modifications that will be recognized by one of ordinary skill in the art.

EXAMPLE 1

1,7-Dihydroxy-2,4,6-trinitro-2,4,6-triazaheptane

To 6.7g of 1,7-diacetoxy-2,4,6-trinitro-2,4,6-triazaheptane (18.9 mmol) was added 33 ml of 30% aqueous HCl. The mixture was then stirred for 48 hours at room temperature. The solid was collected by suction filtration through a sintered glass funnel, washed with distilled water, and dried in vacuo. Collected was 3.9 g (75%); melting point 134°-138° C.; $^1$H NMR spectrum (d$_3$-acetonitrile): δ 5.40 and 5.87.

The method of example 1 can be used to produce 1,9-dihydroxy-2,4,6,8-tetranitro-2,4,6,8-tetraazanonane from 1,9-diacetoxy-2,4,6,8-tetranitro-2,4,6,8-tetraazanonane.

Examples 2 and 3 present prior art methods which were used to prepare the diacetoxymethyl nitramines which can be used as starting materials for preparing the hydroxy terminated nitramines.

Examples 2 and 3 are quoted from page 2772 of an article by W. E. Bachmann, W. J. Horton, E. L. Jenner, N. W. MacNaughton and L. B. Scott, titled, "Cyclic and Linear Nitramines Formed by Nitrolysis of Hexamine," which appeared in the *Journal of the American Chemical Society*, Volume 73, No. 6 (June 1951), pages 2769-2773, herein incorporated by reference in its entirety.

EXAMPLE 2 (PRIOR ART)

1,7-Diacetoxy-2,4,6-trinitro-2,4,6-triazaheptane

"1,7-Diacetoxy-2,4,6-trinitro-2,4,6-triazaheptane (IV).—A series of runs were made in which hexamine, nitric acid and acetic anhydride were brought together under various conditions. In (a) is given a procedure in which ease of obtaining a pure compound rather than yield is emphasized. In (b) is given a procedure which employs hexamine dinitrate.

"(a) Forty-five cc. of 98% nitric acid was added gradually with stirring to 120 cc. of acetic anhydride (in a three-necked flask equipped with a thermometer and a paddle stirrer) which was kept at 15°-20° by means of an ice-bath. A solution of 33.6 g of hexamine in 55 cc. of glacial acetic acid was added continuously to the stirred mixture at 15°-20° in twenty minutes. The resulting mixture was heated in the course of fifteen minutes to 75°; the clear solution was stirred as it cooled to room temperature; at about 70° a few crystals of IV were introduced. After standing at room temperature for twelve hours, the well-formed crystals of IV were collected on a filter and washed with acetic acid. The moist product was dissolved in 100 cc. of hot acetic acid, and the solution after seeding was allowed to cool; yield of colorless plate 43 g. (51%); m.p. 153°-154.5°.

"The original mother liquor contained additional IV and much water-insoluble gum. The whole was disposed of by converting it into water-soluble products by addition of 700 cc. of water followed by simmering on a steam-bath for three to five hours.

"By omitting the heating to 70°, a 48-g. first crop was obtained which gave 34 g of IV with m.p. 154-155 on recrystallization."

(The reference also discloses a method of making this compound from hexamine dinitate.

EXAMPLE 3 (PRIOR ART)

1,9-Diacetoxy-2,4,6,8-tetranitro-2,4,6,8-tetraazanonane

"1,9-Diacetoxy-2,4,6,8-tetranitro-2,4,6,8-tetrazanonane (V). Twenty cc. of acetic acid was placed in a four-necked 1-l flask equipped with a thermometer, paddle stirrer and two burets, and the flask was immersed in an ice-bath. A solution of 33.6 g of hexamine in 55 cc of acetic acid and a cold freshly-prepared mixture (see above) of 21 cc of 98% nitric acid and 60 cc of acetic anhydride were added continuously and equivalently in six minutes to the stirred acetic acid; the temperature of the reaction mixture was kept at 30°. After being stirred at 30° for one-half hour more, the thick mixture was poured into a dry beaker (hood). Acetic anhydride (150 cc) was added to the uncleaned reaction flask; 40 cc of 98% nitric acid was added with cooling, and the four-state reaction product (contained in the beaker) was added in three to five minutes; the temperature was kept at 25°-30°. Acetic anhydride (50 cc) was used to transfer the residual material in the beaker into the reaction mixture.

"The stirred reaction mixture was heated slowly to 70°; brown fumes were evolved and some solid remained undissolved. The bath was removed and the mixture was stirred as it cooled to room temperature. After two hours the product was collected on a filter and washed with acetic acid; yield 41.2 g; m.p. 174°-177°. Recrystallization from 600 cc of acetic acid yielded colorless nacreous plates of V; yield 33.1 g. (32%); m.p. 182.5°-183.5°."

EXAMPLE 4

Preparation of Poly(2,2,3,4,4,5,5-octafluorohexanediol formal-co-2,4,6-trinitro-2,4,6-triazaheptanediol formal)

To a well-stirred mixture of 2.62 g (10 mmol) of 2,2,3,3,4,4,5,5-octafluorohexane-1,6-diol, 2.70 g (10 mmol) of 1,7-dihydro-2,4,6-trinitro-2,4,6,-triazaheptane, 3 mL of dry (4A sieves) sulfolane, and 0.6 g (20 mmol) of trioxane was added dropwise with cooling (ice-water) 5 mL of boron trifluoride etherate. The ice-water bath was removed and the mixture was stirred overnight at room temperature. During this period, the mixture became homogenous. It was then poured into ice-water (15 mL), 20 mL of dichloromethane was added, the mixture was stirred for a few min., 1 mL of 30% aqueous hydrogen peroxide was added, and stirring was continued for 3 hours. The organic layer was separated and stirred for 3 hours with a mixture of 10 mL of 1% aqueous KOH and 1 mL of 30% hydrogen peroxide. The phases were separated and the organic layer was washed with brine. Most of the solvent was removed in vacuo and the residual polymer was triturated with distilled water for 3-4 hours at 40°-50° C. The water was poured off and trituration with fresh distilled water was repeated. The polymer was dissolved in 50 mL of tetrahydrofuran and the solution was added to 300 mL of water with vigorous stirring. The aqueous phase was discarded and the precipitated polymer was dissolved in dichloromethane and stirred with about 5 mL of Silica Gel 60 (EM Science) for 8 hours. The silica gel was filtered off and washed with dichloromethane. The solvent was removed from the combined solutions in vacuo, finally at 60°-70° C. to yield 3.7 g of polymer which was characterized by $^1$H NMR spectroscopy to ascertain absence of sulfolane, dichloromethane, and tetrahydrofuran solvents.

By comparison of the gel permeation chromatogram with that of poly(octafluorohexanediol formal) the molecular weight of the polymer ($M_N$) was estimated to be 2600. The $^1$H NMR spectrum (d$_6$-acetone) showed the expected signals as follows: δ 6.12, double peak, 5.72, 5.65 (nitramine diol signals; total area 73); 5.13, 5.07 (formal signals; total area 30); 4.33, triplet $J_{HF}=15$ hz (fluorodiol signal; total area approximately 45).

EXAMPLE 5

Gumstock preparation from Fluorodiol-Nitraminediol Copolymer

A homogeneous mixture of 1 g of the copolymer prepared as in example 1 ($M_N$ 2600) with 3 g of (2,2,2-fluorodinitroethyl) formal was added to 0.1111 g of Desmodur N-100 polyisocyanate, 0.0316 g of IPDI diisocyanate, and 0.003 g of triphenyl bismuth contained in a beaker. The mixture was stirred until homogeneous and then held at 60° C. until it was cured (about 48 hours).

Obviously numerous modifications and variations of the present invention are possible in light of the above teachings. It is therefore to be understood that within the scope of the appended claims the invention may be practiced otherwise than as specifically described herein.

What is claimed as new and desired to be secured by Letters Patent of the United States is:

1. A method of producing dihydroxy terminated nitramines comprising
    contacting a diacetoxy terminated nitramine that is 1,7-diacetoxy-2,4,6-trinitro-2,4,6-triazaheptane or 1,9-diacetoxy-2,4,6,8-tetranitro-2,4,6,8-tetraazanonane with a concentrated aqueous hydrochloric acid comprising from 28 to 32 percent by weight hydrogen chloride with the remainder being water at ambient temperature until the diacetoxy terminate nitramine is hydrolyzed to form the corresponding dihydroxy terminated nitramine, 1,7-dihydroxy-2,4,6-trinitro-2,4,6-triazaheptane or 1,9-dihydroxy-2,4,6,8-tetranitro-2,4,6,8-tetraazanonane, respectively.

2. The method of claim 1 wherein the concentrated aqueous hydrochloric acid comprises from 29 to 31 percent by weight hydrogen chloride with the remainder being water.

3. The method of claim 2 wherein the concentrated aqueous hydrochloric acid comprises about 30 percent by weight of hydrogen chloride with the remainder being water.

4. The method of claim 1 wherein the diacetoxy terminated nitramine starting material is 1,7-diacetoxy-2,4,6-trinitro-2,4,6-triazaheptane.

5. The method of claim 1 wherein the diacetoxy terminated nitramine starting material is 1,9-diacetoxy-2,4,6,8-tetranitro-2,4,6,8-tetraazanonane.

* * * * *